(12) United States Patent
Higginbottom et al.

(10) Patent No.: US 6,465,582 B1
(45) Date of Patent: Oct. 15, 2002

(54) POLYOXAZOLINE COMPOUNDS AND THEIR USE IN SURFACE COATING COMPOSITIONS

(75) Inventors: Harold P. Higginbottom, Wilbraham; Ronald M. Gurge, Needham; Ping Yuan, Amherst, all of MA (US)

(73) Assignee: Solutia Inc., St. Louis, MO (US)

( * ) Notice: Subject to any disclaimer, the term of this patent is extended or adjusted under 35 U.S.C. 154(b) by 0 days.

(21) Appl. No.: 09/831,067

(22) PCT Filed: Nov. 2, 1999

(86) PCT No.: PCT/US99/25645
§ 371 (c)(1),
(2), (4) Date: Aug. 14, 2001

(87) PCT Pub. No.: WO00/26196
PCT Pub. Date: May 11, 2000

(51) Int. Cl.$^7$ ............................ C08F 20/00; B32B 15/02
(52) U.S. Cl. ......................... 525/440; 525/437; 528/59; 528/80; 528/83; 528/405; 528/423; 428/402
(58) Field of Search ................................ 525/437, 440; 528/59, 80, 83, 405, 423; 428/402

(56) References Cited

U.S. PATENT DOCUMENTS

| 3,996,237 A | * | 12/1976 | Tomalia | 526/260 |
| 4,474,942 A | * | 10/1984 | Sano et al. | 524/606 |
| 4,561,225 A | * | 12/1985 | Gartner | 165/50 |
| 4,593,103 A | * | 6/1986 | Johnson | 544/88 |
| 4,731,398 A | * | 3/1988 | Huber et al. | 525/111 |
| 4,737,410 A | * | 4/1988 | Kantner | 523/501 |
| 5,635,571 A | * | 6/1997 | Frechet et al. | 525/410 |

FOREIGN PATENT DOCUMENTS

| FR | 1487711 | * | 5/1967 |
| WO | WO 00/26196 | * | 5/2000 |

\* cited by examiner

*Primary Examiner*—Samuel A. Acquah
(74) *Attorney, Agent, or Firm*—Howrey Simon Arnold & White, L.L.P.

(57) ABSTRACT

Polyoxazoline compounds useful as crosslinkers in liquid or powder surface coating compositions which contain at lest four, for example six, oxazoline or substituted oxazoline functional groups which react with carboxyl functionality of a coreactive polymer of the coating composition are disclosed.

9 Claims, No Drawings

POLYOXAZOLINE COMPOUNDS AND THEIR USE IN SURFACE COATING COMPOSITIONS

This invention relates to multi-functional oxazoline compounds and more particularly to surface coating compositions containing these compounds as crosslinkers.

Thermoset surface coatings containing crosslinkers and coreactants are well known. The chemical structure of the crosslinker composition influences the end-use application of the coating, such as the bake temperature and time for curing. For example, small, highly functional molecules are desirable crosslinkers in liquid coatings since high solvent levels to reduce viscosity are avoided—i.e. the coatings can have high solids and low viscosity thereby keeping VOC levels and the energy required to evaporate solvent low to minimize environmental pollution. Small crosslinker molecules in powder coatings improve melt rheology prior to curing—i.e. after spraying the powder coating on the substrate and prior to gelation at elevated temperature, the small solid crosslinker molecules readily melt and flow thereby directly contributing to an attractive appearance of the final powder coating. In chemically designing such crosslinkers, the balance between cost and performance is also a factor. Desirable commercial properties of the coating include UV insensitivity, good adhesion to metal and other coating substrates and the absence of volatile emissions such as water or organics during cure. The latter is especially important in powder coatings to avoid disrupting the finished powder film coating.

SUMMARY OF THE INVENTION

New molecules have been designed which usefully satisfy the foregoing requirements for crosslinkers in surface coating compositions.

Accordingly, a principal object of this invention is to provide low molecular weight (less than 1000) molecules having multi-functional sites available to participate in reactions with other chemical components.

Another object is to provide such polyfunctional molecules in which such multi-functional sites are particularly capable of crosslinking carboxyl functional coreactants of coating compositions.

An additional object is to provide cured coatings having high crosslink density and a balance of performance properties which includes resistance to UV exposure for outdoor applications.

A specific object is to provide multi-functional molecules which are particularly designed for crosslinking use in powder coating formulations.

Other objects will in part be obvious and will in part appear from the following description and claims.

These and other objects are accomplished by providing a compound of the formula:

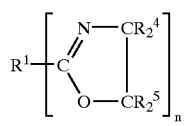

(1)

where n is 4 or 6; $R^1$ is a tetravalent or hexavalent group of the formula:

$(CR_2^2CR_2^2)_2NCOR^3OCN(R_2^2CR_2^2C)_2;$ where $R^2$ is H or $C_1$ to $C_6$ linear or branched alkyl; $R^3$ is selected from: $(CH_2)_x$ and its branched isomers where x is 1 to 20; —$C_6H_{10}$—; and

$—(CH_2)_2CHNCO(CR_2^2CR_2^2)_{-2}(CH_2)_{-3};$ and $R^4$ and $R^5$ are each H or $CH_3$.

Also provided is a curable coating composition containing a carboxyl-functional coreactant polymer such as polyester and the polyoxazoline compound of formula (1) above as crosslinker wherein during curing the rings of the oxazoline groups react with the carboxyl functionality of the coreactant by ring opening.

DETAILED DESCRIPTION OF THE INVENTION

Polyoxazoline compounds of formula (1) are formed by reactively coupling iminodialkylnitriles (e.g. 3,3$^1$-iminodipropionitrile (IDPN) with a difunctional or trifunctional aliphatic polycarboxylic acid or polycarboxylic acid derivatives such as adipoyl chloride as coupling agents which react with the imino group (secondary amine) of the iminodialkylnitrile forming polyfunctional (i.e. tetra or hexa) nitrile intermediates which, in a subsequent step, are converted to tetra or hexa-substituted polyoxazolines by reacting each nitrile group with a monoethanolamine group. The iminodialkylnitrile intermediate may be obtained commercially or prepared as just noted. IDPN is synthesized from readily available raw materials by reacting 2 moles of acrylonitrile (AN) or methyl or dimethyl substituted acrylonitrile with ammonia according to the following reaction (using unsubstituted AN):

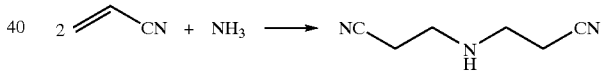

IDPN prepared by this reaction is described in Example 1, Part A of U.S. Pat. No. 3,444,137 to Higginbottom et al. The iminodialkylnitrile intermediate is of formula

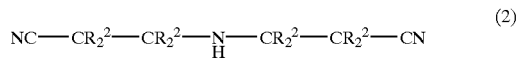

(2)

where $R_2$ is selected from H (i.e. IDPN) or $C_1$ to $C_6$ linear or branched alkyl.

The coupling agent for reaction with the reactive H of the imino group of the iminodialkylnitrile intermediate is aliphatic di or tri carboxylic acid or di or tri acid derivative thereof of the formula

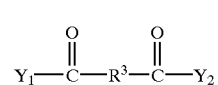

(3)

where $Y_1$ and $Y_2$ are each selected from hydroxyl (i.e. the diacid) and halogen which includes fluorine, chlorine and bromine with chlorine being a preferred halogen (i.e. the acid chloride derivative) $Y_1$ and $Y_2$ react with the imino hydrogen in the coupling reaction forming $H_2O$ or H-halogen—e.g. HCl. $R^3$ of the coupling agent is selected from $(CH_2)_x$ and its branched isomers where x is 1 to 20;

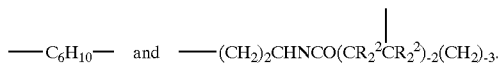

The latter group is based on 1,3,6-hexanetricarboxylic acid.

The final step in synthesizing polyoxazoline compounds of formula (1) is the reaction of ethanolamine with the iminodialkylnitrile intermediate product of the coupling reaction described above. In this reaction each CN group of the intermediate is converted to an oxazoline group of the formula within the brackets in (1). For example, tetraoxazoline of formula (1) from one mole of tetranitrile intermediate (from IDPN and adipoyl chloride) and 4 moles of ethanolamine is formed according to the following reaction:

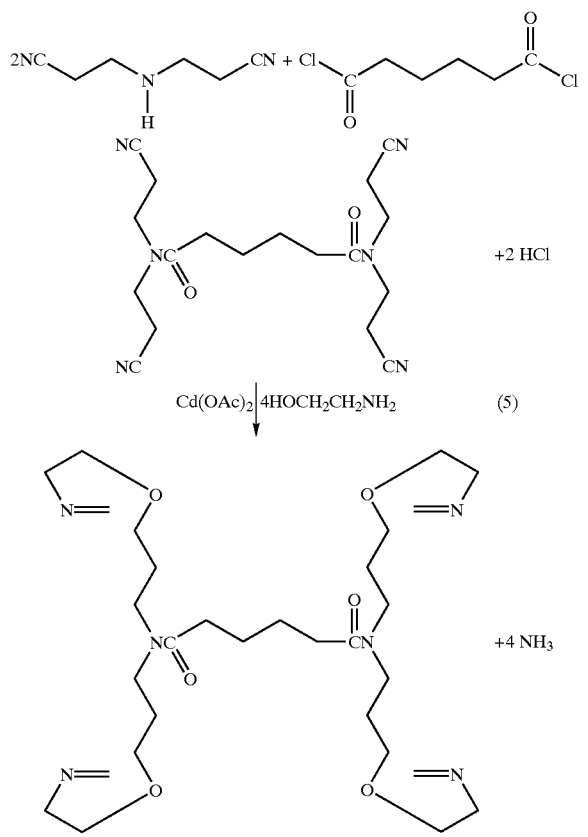

The polyoxazoline compounds of the invention are usable as crosslinkers in liquid and powder coating compositions. They are highly functional from the presence of 4 or 6 oxazoline rings reactive toward carboxyl groups of a coreactant by ring opening of the oxazoline groups. Such polyoxazolines of the invention are high purity, crystalline compounds having a sharp melting point to facilitate incorporation into powder coating systems. For liquid coatings, the crosslinker usable in powders is dissolved in an appropriate solvent known to skilled coating artisans. Oxazoline functionality is achieved in such non-polymeric compounds with relatively low (e.g. 450–1000) molecular weight by choice of the coupling agent in the coupling reaction to define the backbone structure of the compounds ($R^1$ in formula (1)). High molecular weight polyoxazolines are less desirable as crosslinkers because they increase solution viscosity of liquid applied coatings or melt viscosity of powder coatings. The former affects VOC and the latter affects appearance. Moreover, the invention polyoxazolines are aliphatic (as opposed to aromatic) compounds to provide UV stability and avoid degradation of the coatings in outdoor applications.

The species of polyoxazoline crosslinkers of the invention with methyl substituents on the oxazoline rings ($R^4$ and $R^5$ in formula (1) are $CH_3$) are less reactive in the curing reaction than those with unsubstituted rings ($R^4$ and $R^5$ are H). This change of reactivity with constituents on the rings can be exploited in formulating powder coatings of different reactivities; e.g. use the less reactive methyl substituted oxazoline species in formulations with bake temperatures greater than about 150° C. whereas the more reactive unsubstituted species would be used with formulations for low and high temperature cure applications. The less reactive substituted species can be used over a broader range of processing conditions without premature reaction.

In forming a surface coating from the curable coating composition of the invention, the carboxyl group of a carboxyl-functional coreactant reacts with and opens an oxazoline ring of the polyoxazoline crosslinker to form an ester-amide crosslink structure in the cured coating. This addition reaction importantly avoids liberating any byproducts (including disfavored volatiles) and is illustrated by the following reaction where $R^1$ is defined as in formula (1) and R is the backbone of the coreactant.

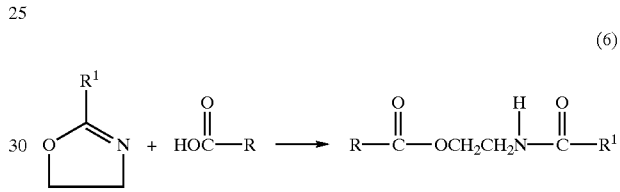

The oxazoline-containing crosslinker has no strong hydrogen bonding sites present which desirably contributes to low melt viscosity and high flow. Upon cure and formation of ester-amide crosslinks, strong hydrogen bonding functionality does exist which can desirably contribute to adhesion to substrates.

A form of carboxyl functional coreactant polymer usable in curable coating compositions of the invention is a polyester resin having an average of two or more carboxyl groups. such polyester resins are obtained by the condensation reaction between a polyol component and a polyfunctional acid component. The equivalents of acid are in excess so an acid-functional polyester resin has an acid number of 18 to 60 mg KOH/g. and a Tg of 50 to 60° C. The viscosity of the polyester as measured at 200° C., is preferably from 1000 to 70000 mPa.S.

The poly-functional acid component comprises compounds having two or more carboxyl groups or their anhydrides. Such compounds may be alkyl, alkylene, aralkylene, or aromatic compounds. Dicarboxylic acids and anhydrides are preferred. Acids or anhydrides with higher functionality may be used where some branching of the polyester is desired. When tri-functional or higher functionality compounds are used, it is possible to include mono-functional carboxylic acids or anhydrides or anhydrides of monocarboxylic acids, such as versatic acid, fatty acids, or neodecanoic acid, so long as the poly-functional acid component has an average functionality of at least two.

Examples of compounds having two or more carboxyl groups or anhydrides of such compounds include phthalic acid, phthalic anhydride, isophthalic acid, terephthalic acid, hexahydrophthalic acid, tetrachlorophthalic anhydride, hexahydrophthalic anhydride, pyromellitic anhydride, succinic acid, azeleic acid, adipic acid, 1,4-cyclohexanedicarboxylic acid, citric acid, and trimellitic anhydride.

The polyol component used to make the polyester resin also has average functionality of at least two. The polyol component may contain mono-, di-, and tri-functional alcohols, as well as alcohols of higher functionality. Diols are preferred polyols. Alcohols with higher functionality may be used where some branching of the polyester is desired, and mixtures of diols and triols are also preferred polyols.

Examples of useful polyols are ethylene glycol, diethylene glycol, propylene glycol, dipropylene glycol, butylene glycol, glycerine, trimethylolpropane, trimethylolethane, pentaerythritol, neopentyl glycol, 2,2,4-trimethyl-1,3-pentanediol, 1,6-hexanediol, 1,4-cyclohexane dimethanol, hydrogenated bisphenol A, and hydroxyalkylated bisphenols.

Methods of making polyester resins are known. Polyesters are typically formed by heating the polyol and polyfunctional acid components together, with or without catalysis, while removing water by-product to drive the reaction to completion. A small amount of a solvent, such as toluene, may be added to remove the water azeotropically. Such solvent is preferably removed from the polyester product before beginning coating formulation.

Many polyester resins are commercially available as 100% solids usable in powder coating compositions, such as those sold by Hoechst, Portsmouth, Va. 23704, under the tradename Alftalat; by EMS-American Grilon, Inc., Sumter, S.C. 29151, under the tradename Grilesta; by CIBA-Geigy Corporation, Ardsley, N.Y. 10502, under the tradename Arakote; by Ruco Polymer Corp., Hicksville, N.Y. 11820 under the tradename Rucote; by McWhorter Technologies, Carpentersville, Ill. 60110 under the tradename Albester. Also Uralac® resins from DSM Resins International.

Another usable carboxyl functional polymer is acrylic copolymer which is preferably amorphous and has a number average molecular weight of 500 to 4000, Tg of 30 to 100° C. and acid number of about 40 to 240.

The carboxyl functional acrylic copolymer is prepared from acrylic acid and/or methacrylic acid ester monomers and ethylenically unsaturated carboxyl functional-group containing monomers. Other ethylenically unsaturated copolymerizable monomers may also be present. Preferably, the carboxyl functional-group containing acrylic copolymer comprises 20 to 95 percent by weight of at least one acrylic or methacrylic acid ester monomer having 1 to 20 carbon atoms, 5 to 30 percent by weight of at least one ethylenically unsaturated carboxyl functional-group containing monomer, and 0 to 60 percent by weight of at least one other ethylenically unsaturated copolymerizable monomer, based on the total weight of the monomers.

Examples of acrylic acid ester monomers include methyl acrylate, ethyl acrylate, n-propyl acrylate, isopropyl acrylate, n-butyl acrylate, and n-decyl acrylate. Examples of methacrylic acid ester monomers include methyl methacrylate, ethyl methacrylate, n-propyl methacrylate, n-butyl methacrylate, isopropyl methacrylate, isobutyl methacrylate, n-amyl methacrylate, n-hexyl methacrylate, isoamyl methacrylate, allyl methacrylate, sec-butyl methacrylate, tert-butyl methacrylate, 2-ethylbutyl methacrylate, cinnamyl methacrylate, crotyl methacrylate, cyclohexyl methacrylate, cyclopentyl methacrylate, methallyl methacrylate, n-octyl methacrylate, 2-ethylhexyl methacrylate, 2-phenylethyl methacrylate, and phenyl methacrylate.

Examples of ethylenically unsaturated carboxyl functional group containing monomers include acrylic acid, methacrylic acid, crotonic acid, itaconic acid, fumaric acid, maleic acid, citraconic acid, and monoalkyl esters of unsaturated dicarboxylic acids. Preferred ethylenically unsaturated carboxyl functional group containing monomers are acrylic acid and methacrylic acid.

Examples of other ethylenically unsaturated copolymerizable monomers include vinyl aromatic monomers, such as styrene, alkyl-substituted styrenes, and chloro-substituted styrenes; nitriles, such as acrylonitrile; vinyl and vinylidene halides, such as vinyl chloride and vinylidene fluoride; and vinyl esters, such as vinyl acetate.

The acrylic copolymer is made by conventional free radical initiated polymerization.

Suitable usable free radical initiators include benzoyl peroxide, tert-butyl hydroperoxide, ditert-butyl peroxide, azobis (2-methylpropionitrile. Other known techniques such as emulsion, suspension and bulk polymerization may also be used to make the acrylic copolymer.

Commercially available acrylic copolymers useful in coating compositions of the invention are sold by S. C. Johnson, Racine, Wis. 53403 under the tradename Joncryl®, types 815, 817 and 819 and, for liquid coatings, by McWhorter Technologies, Inc., Carpentersville, Ill. 60110 under the tradename Acrylamacs®.

With liquid coating compositions containing the polyoxazoline crosslinker(s) of the invention, the composition may either be a "one-pack" or "two-pack" system. With a one-pack system, the components have long shelf life and need not be kept separate from each other before application as does a two-pack system. The coatings prepared in Examples 4–7 hereafter need to be applied to the substrate within a few hours after mixing of the components. For a one-pack system using the inventive polyoxazolines, the carboxyl-functional coreactant should be present as the amine-neutralized carboxyl-functional coreactant. The amine blocking group is eliminated as a volatile during cure.

The carboxyl functional coreactant polymer and crosslinker are apportioned in the curable coating composition so that the equivalents of coreactant to the equivalents of crosslinker are in a ratio of 0.8 to 1.5:1, preferably about 1:1.

The amount of coreactant in the coating composition is 80 to 98 preferably 88 to 95% by weight based on total weight of coreactant and crosslinker. The crosslinking agent, therefore is present at between 2 to 30, preferably (for powder coatings) about 5 to 12% by weight and for liquid coatings preferably about 10 to 25% by weight. On an equivalent basis the amount of coreactant is similar for liquids and powders. The weight ratio is determined by the equivalent ratio used.

Processing and performance additives are optionally incorporated into the coating composition. These include fillers, pigments, leveling agents to help coalesce the coating film, plasticizers, flow control agents to smooth the film, air release agents, hindered amine light stabilizers, ultraviolet light absorbers, antioxidants, and catalysts. Particularly recommended for powder coatings are degassing agents which allow volatiles to escape from the film during baking and flow control agents to prevent cratering. Benzoin is a preferred degassing agent.

Pigments are used in amounts of 0 to 35% by weight, based on total weight of the coating composition. The pigments may be inorganic, including metal oxides, chromates, molybdates, phosphates, and silicates. Also titanium dioxide, barium sulfate, carbon black, ocher, sienna, umber, hematite, limonite, red iron oxide, transparent red iron oxide, black iron oxide, brown iron oxide, chromium oxide green, strontium chromate, zinc phosphate, silicas such as fumed silica, talc, barytes, ferric ammonium ferrocyanide (Prussian blue), ultramarine, lead chromate, lead molybdate, and mica flake pigments. Organic pigments include metallized azo reds, quinacridone reds and violets, perylene reds, copper phthalocyanaine blues and greens, carbazole violet, monoarylide and diarylide yellows, benzimidazolone yellows, tolyl orange, naphthol orange, and the like.

Flow control agents prevent formation of dirt craters by reducing surface tension. Dirt cratering is caused by dirt falling on the coating before it is cured. Flow control agents are generally nonfunctional, low Tg polymers, such as acrylic or siloxane polymers or fluorinated polyesters. Examples include polylauryl acrylate, polybutyl acrylate, poly(2-ethylhexyl) acrylate, polylauryl methacrylate, poly (dimethylsiloxane), and esters of polyethylene glycol or polypropylene glycol and fluorinated fatty acids.

Flow control agents are used in very low amounts. When the amount exceeds about 2% the coating tends to degrade in appearance and other properties. A primer coating using more than about 2% of flow control agent exhibits poor intercoat adhesion to a topcoat applied subsequently in the coating process.

Hindered amine light stabilizers, ultraviolet light absorbers, and antioxidants may be added in ways and amounts known to the art to improve the durability of the finished coating, particularly for outdoor applications.

Thermoset powder coating compositions can be prepared by first melt blending the ingredients. This usually involves dry blending in a planetary mixer and then melt blending the admixture in an extruder at elevated temperature. The extrusion temperature is high enough to allow the resin to melt to a viscosity that produces good mixing and pigment wetting, but is not so high that any significant amount of coreaction between resin and crosslinker occurs. Such melt blending is usually carried out from 60° C. to 130° C.

The melt blended extrudate is then cooled and pulverized. The extrudate may be crushed to a fine flake or granule and then ground and classified by sieving or other means. The maximum particle size and the particle size distribution are controlled in the classifying step and affect the smoothness of the final powder coating film.

Requirements for these parameters depend upon the particular use and application method.

Alternatively to the foregoing, one or all of the powder formulation components may be dry blended into a powder formulation without extrusion.

Thermoset powder coating compositions can be applied to many different substrates, including metal substrates such as bare steel, phosphatized steel, galvanized steel, or aluminum; and non-metallic substrates, such as plastics and composites. The substrate may already have a layer of another coating, such as a layer of an electrodeposited primer, cured or uncured, applied before applying the powder coating composition. In a preferred embodiment, the substrate is an automotive body.

Application can be by electrostatic spraying or by use of a fluidized bed. Electrostatic spraying is the preferred method. The coating powder can be applied in one or more passes to provide a coating film thickness after cure of from 25 to 400 microns, but when used as an automotive primer, coating thickness is generally from 50 to 250 microns. The substrate can optionally be preheated before applying the powder coating composition to promote uniform and thicker powder deposition.

After applying the composition to a substrate the coating is cured, preferably by heating at a temperature and for a length of time sufficient to cause the reactants to form an insoluble polymeric network. The cure temperature for powder coatings is usually 120 to 205° C. for a length of cure of 15 to 60 minutes. Preferably the powder coating is cured at 170 to 180° C. for 20 to 30 minutes. Usually this is the temperature range used for most commercial powders although powder coatings of this invention can often be cured below 150° C. With liquid coatings, curing is usually at 100 to 150° C. for about 20 to 30 minutes or at higher temperature for a shorter time—e.g. about 200° C. for 2 min.

Exemplary of the invention are the following specific Examples wherein amounts and percentage are expressed by weight.

EXAMPLE 1

Preparation of Tetraoxazoline Via Adi-poyl Coupled IPDN

A) Tetranitrile Via Coupling Reaction

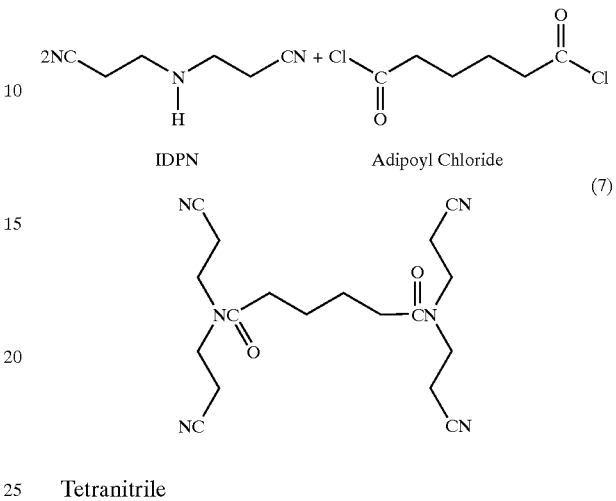

Tetranitrile

| Reaction Components | Wt. (gm) |
|---|---|
| 3,3'-Iminodipropionitrile (IPDN) [Aldrich, tech., 90%] | 86.0 |
| Adipoyl Chloride (ADC) [Aldrich, 98%] | 68.0 |
| Triethylamine (TEA) (ET$_3$N) [Aldrich, 99%] | 74.4 |
| Acetonitrile (Solvent) (CH$_3$CN) [Aldrich, 99.7%] | 140 |

IPDN, acetonitrile and TEA are charged to a 500 cc reactor. The reaction solution is cooled to 0.5° C. and an inert nitrogen atmosphere maintained in the reactor. With continuous stirring and cooling, ADC is added dropwise over 1.5 hours keeping the temperature below 10° C. A white precipitate forms during addition of ADC and the addition of more acetonitrile may be required to keep the slurry stirrable. When addition of ADC is complete, the slurry is stirred with cooling for an additional ½ hour and then allowed to warm to room temperature. The slurry is filtered and washed twice with methanol. The washed white solid is dried in a vacuum oven at 60° C. at 29" Hg vacuum. $^{13}$CNMR analysis shows 98+% pure tetranitrile compound named N,N,N$^1$,N$^1$,-tetrakis-(2-cyanoethyl)adipamide. Yield of the adipate-coupled tetranitrile intermediate is 90–95%.

B) Tetraoxazoline-substituted Crosslinker Refer to Reaction (5) Above

| Reaction Components | Wt. (gm) |
|---|---|
| Tetranitrile [adipoyl coupled IDPN] | 95 |
| n-Butanol (solvent) (99.4% reagent grd.] | 180 |
| Toluene (solvent) [99.5% reagent] | 10 |
| Cd (OAc)$_2$2H$_2$O (Aldrich, 98%] | 7.0 |
| Ethanolamine | 70 |

-continued

| Reaction Components | Wt. (gm) |
|---|---|
| [Aldrich, 99+%] | |
| Ethylene diamine tetra-acetic acid (EDTA) salt sol. #1 | 50 |
| NaCl Saturated wash sol. #2 | 25 |

Sol. #1 is 8 parts EDTA, 7 parts aqueous ammonia (29%), 30 parts NaCl, 55 parts $H_2O$. Sol. #2 is a saturated aqueous salt solution of NaCl. Tetranitrile from A) above is slurried in a 500 cc reactor with the n-butanol and toluene solvents. An inert nitrogen atmosphere is maintained in the reactor. Under agitation, the reaction mixture is heated to atmospheric azeotropic reflux. Water is removed from the reaction medium over about ½ hour. After azeotropic water removal the reaction temperature is adjusted to 115–120° C. and the ethanolamine added slowly over 2 hours while keeping reaction temperature at 120° C. The heterogeneous reaction slurry becomes clear and homogeneous during addition of ethanolamine. After ethanolamine addition is complete, the reaction is held at 120° C. until the nitrile group essentially disappears (about 6 hours in present example). This is determined by sample analysis using FTIR spectroscopy (IR absorbance at 2250 wave numbers).

The reaction is cooled to room temperature and the clear reaction solution washed with sol. #1 and the wash solution removed (lower layer). The reaction product is then washed with sol. #2, followed by removal of the aqueous salt layer. The clear organic layer is dried over anhydrous sodium sulfate, filtered and then the solvents are removed at 70° C. and 28–29" of Hg vacuum. The stripped reaction product is recrystallized from ethyl acetate and dried in a vacuum oven at 60° C. and maximum vacuum. The combined 1st and 2nd crystal crops give 60% yield of pure (98+% using $^{13}CNMR$) tetraoxazoline with a melting point in the range of 104–109° C., named $N,N,N^1,N^1$-tetrakis[2-(2-oxazolinyl)-ethyl] adipamide.

EXAMPLE 2

Tetraoxazoline Using Dodecanedioyl Chloride

The procedure of Example 1 is repeated except adipoyl chloride is replaced on a molar basis with dodecanedioyl chloride which is available commercially from Aldrich Chemical. The melting point of the tetraoxazoline product is 105 to 109° C. Chemical name is $N,N,N^1,N^1$-tetrakis[2-(2-oxazonyl)-ethyl]dodecanedioamide.

EXAMPLE 3

A) Tetra 5-methyloxazoline

The procedure of Example 1 is repeated except using 1-amino-2-propanol instead of ethanolamine (same molar basis) in the oxazoline ring-forming reaction. Each oxazoline ring of the tetraoxazoline product is methyl substituted and of the formula:

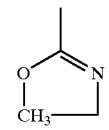

B) Tetra 4,4' dimethyloxazoline

The procedure of Ex. 3A) is repeated except using 2-amino-2-methyl-1 propanol instead of 1-amino-2-propanol in the oxazoline ring-forming reaction. Each oxazoline ring of this tetraoxazoline product is dimethyl substituted and of the formula:

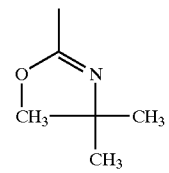

EXAMPLES 4–7

Preparation of Crosslinked Liquid Coatings

Liquid coating compositions using the polyoxazoline compounds of Exs. 1–3 as crosslinkers are prepared and identified in Table 1. The tetraoxazoline is identified by block letter in the Table and described in the lettered footnote below the Table. Each tetraoxazoline in these Examples is a crystalline solid dissolved in the solvent noted.

TABLE I

| | EXAMPLE | | | |
|---|---|---|---|---|
| Components | 4 | 5 | 6 | 7 |
| Tetraoxazoline [Solids] | A[22] | B[25] | C[24] | D[26] |
| Parts 50% Solution in (Solvent) | 44(butanol) | 50(butyl cellosolve) | 48(butanol) | 52(butanol) |
| McWhorter 17-724[1] Acrylamac ® [Solids][1] | [78] | [75] | [76] | [74] |
| Parts 75% solids | 104 | 100 | 103 | 98.7 |
| Modaflow ®[2] [Solids] | [0.5] | [0.5] | [0.5] | [0.5] |
| Parts 50% in xylene | 1 | 1 | 1 | 1 |
| Component Equivalence Ratio | 1.08/1.0 | 1.1/1.0 | 1.1/1.0 | 1.05/1.0 |

TABLE I-continued

| | EXAMPLE | | | |
|---|---|---|---|---|
| Components | 4 | 5 | 6 | 7 |
| Oxazoline/Acrylic COOH | | | | |

[1]Carboxyl functional acrylic coreactant polymer resin available from McWhorter Technologies Inc. as 75% solids in a mixed n-butanol/Ektasolve FP 60:40 solvent. Acid equivalent weight on solids 510.
[2]Available from Solutia Inc., St. Louis, MO
A = unsubstituted oxazoline ring-adipoyl coupled
B = unsubstituted oxazoline ring-dodecanedioyl coupled
C = methyl substituted oxazoline ring-adipoyl coupled
D = 4,4[1]-dimethyl substituted oxazoline ring-adipoyl coupled Cure profile comparisons are made using a BYK Chemie Gradient Oven. ACT cold roll steel test panels (4"×22.5"×0.032 or 10.2 cm×57 cm×0.08 cm-B1000, P60, D1W, polished) are used as substrates. A 3"(7.6 cm) wide film is draw coated the length of the test panel using a doctor blade and the BYK Chemie Applicator Tool. Blade size is selected to give a cured film of about 1.2 mil (0.03 mm) thick on the test panel. Wet films after draw coating are dried at room temperature for 30 min. prior to cure in the Gradient Oven. The oven is programmed to give four constant temperature cure zones 4" (10 cm) in length for each cure cycle. Each cure zone is separated by a 0.75" (1.9 cm) buffer zone at 40° C.

Film Test Procedures

1) Solvent Resistance by the methyl ethyl ketone (MEK) double-rub test. MEK is placed in a hollow-barreled felt tip marker and one back and forth stroke made across the film per second. A reported value less than 200 is the number of double rubs required to remove the coating down to the substrate within the stroke path. The test is stopped at 200 double rubs even if the coating is still present. If no film removal or marring at the stopping point, the value is reported as 200+. If some film marring, scratching or gloss loss at the stopping point, the value is reported as 200 (M).

2) Impact Resistance is measured with a Gardner Impact Tester® as described in ASTM D2794 using a 1.27 cm diameter ball. 160 inch pounds or greater forward impact is usually obtained with polyester coreactants; acrylic coreactants may give lower impact resistance values depending on the specific acrylic coreactant.

Cured coating results obtained are as follows:
Baked Film Property Results

| | Bake Temperature (C.) (30 min. at indicated temp.) | | | | | | | | | | |
|---|---|---|---|---|---|---|---|---|---|---|---|
| Example | 65 | 79 | 93 | 107 | 121 | 135 | 140 | 149 | 163 | 177 | 199 |
| Solvent Resistance (MEK Double Rubs) | | | | | | | | | | | |
| 4 | | 14 | 14 | 50 | 200+ | 200+ | 200+ | 200+ | 200+ | 200+ | 200+ | 200+ |
| 5 | | | 200+ | 200+ | 200+ | 200+ | 200+ | 200+ | 200+ | 200+ | 200+ |
| 6 | 5 | 5 | 5 | 10 | 10 | 25 | 70 | 140 | 200+ | 200+ | 200+ |
| 7 | 5 | 5 | 5 | 5 | 5 | 5 | 5 | 10 | 20 | 140 | 160 |
| Forward Impact Resistance (inch-lbs) | | | | | | | | | | | |
| 4 | | 15 | 20 | 45 | 160 | 160 | 160 | 160 | 160 | 160 | 160 | 160 |
| 5 | | | 40 | 100 | 140 | 160 | 160 | 160 | 160 | 160 | 160 |
| 6 | 5 | 5 | 5 | 10 | 10 | 15 | 15 | 35 | 65 | 160 | 160 |
| 7 | 5 | 5 | 5 | 5 | 5 | 5 | 5 | 10 | 20 | 140 | 160 |

EXAMPLES 8–13

Preparation Of Crosslinked Powder Coatings

Powder coatings were prepared and evaluated as follows. The dry formulation components are premixed and ground in a Waring Blender. The ground powder is fed to an extruder (Buss-Kneader PCS-30) with a barrel temperature of 60° C. turning at 300 rpm. The extrudate is cooled, ground and sieved. The sieved fraction smaller than 105 microns is collected as the powder coating. This coating is electrostatically sprayed onto ACT cold roll steel test panels (4"×22.5"×0.032-B100, P60, DIW, polished). The panels are cured in a BYK Chemie Gradient Oven for 30 minutes at a continuous gradient temperature profile of 125–225° C. The temperature where 200 double rub solvent resistance is first obtained is shown in Table 2. Film thickness is controlled at 1.7 to 2.4 mils.

The tetraoxazoline used in the coating formulations of these Examples bears the same block letter and identity as shown in Table I of the prior liquid coating Examples 4–7.

| | EXAMPLE | | | | | |
|---|---|---|---|---|---|---|
| Components | 8 | 9 | 10 | 11 | 12 | 13 |
| Rucote 911[1] | 90.2 | | | | 89.8 | |
| Albester 630-5570[2] | | 92.2 | 91.5 | 89.7 | | 91.5 |
| Tetraoxazoline | | | | | | |
| A | 9.8 | 7.8 | | 10.3 | | |
| B | | | 8.5 | | | |
| C | | | | | 10.2 | 8.5 |
| Benzoin[3] | 0.5 | 0.5 | 0.5 | 0.5 | 0.5 | 0.5 |
| Modaflow | 0.5 | 0.5 | 0.5 | 0.5 | 0.5 | 0.5 |

[1]Carboxyl-functional polyester resin from Ruco Polymer Corp. acid equiv. wt. = 1250.
[2]Carboxyl-functional polyester resin from McWhorter Technologies Inc., acid equiv. wt. = 1735.
[3]Anti-pinhole agent from Rhone-Poulenc Inc.

TABLE 2

| Example | Bake Temperature (° C.) to Reach 200 Double Rubs - 30 Minute bake time |
|---|---|
| 8 | 180 |
| 9 | 180 |
| 10 | 184 |
| 11 | 164 |
| 12 | >220 |
| 13 | 184 |

EXAMPLES 14–19

Preparation of Powder Formulation Blends

Powder coating formulations were prepared and evaluated as follows. Each formulation component (defined in table below) was ground separately to a fine powder in a Waring Blender. The separately ground components were combined as powders in the ratios indicated and roll blended until a uniform powder blend resulted. The powder blends were then compared for gel times on two cure plates regulated at 135° C. and at 200° C. respectively. Gel times were measured using a 10 mm flat spatula with rounded end to apply and work the powder. Approximately 0.1 gm of powder blend was placed in the center of the cure plate and when melted it was worked in a circular motion with the spatula, keeping the area covered by the melted powder to an approximate 2.5–4.0 mm diameter. Movement of the spatula, with slight pressure on the melted powder mixes the different components together so the melt is homogeneous. The spatula is kept in contact with the resin surface and periodically moved circularly until the gel point is reached. The gel point is determined by periodically lifting the spatula 25–50 mm from the resin surface. The resin will string between the hot plate and raised spatula until the gel point is reached. At the gel point stringing stops and the film is usually rubbery or not tacky. The time between applying the resin to the hot plate and when it gels is measured in seconds and recorded as gel time of the powder formulation. The gel time is an average of two or more repetitive measurements. At the gel point the coating formulation has begun the cure stage. Further curing will occur with time.

The crosslinkers used in these blended powder coating formulations were the tetraoxazoline of Example 1 and commercially available crosslinkers Araldite PT 810 and Primid XL-552. Coating formulations using these crosslinkers with a commercial carboxylated polyester resin (Uralac P5700) are shown in Examples 14–19 with hot plate gel times in seconds shown in Table 3. Examples, 14, 15 and 16 are unpigmented formulations whereas 17–19 contain TiO2 pigment to examine the effect of pigment on cure.

| | EXAMPLE | | | | | |
|---|---|---|---|---|---|---|
| Components | 14 | 15 | 16 | 17 | 18 | 19 |
| Tetraoxazoline[1] | 8.00 | — | — | 8.00 | — | — |
| Araldite PT810[2] | — | 7.00 | — | — | 7.00 | — |
| Primid XL-552[3] | — | — | 5.40 | — | — | 5.40 |
| Uralac P5700[4] | 92.00 | 93.00 | 94.60 | 92.00 | 93.00 | 94.60 |
| Ti-Pure 960[5] | — | — | — | 50.00 | 50.00 | 50.00 |
| Modaflow[6] | 0.5 | 0.5 | 0.5 | 1.50 | 1.50 | 1.50 |

[1]Tetraoxazoline prepared according to Example 1. Ave. equiv. wt. (e.w.) = 133
[2]Triglycidyl isocyanurate (TGIC) from Ciba-Geigy Corp. Ave. e.w. = 106
[3]Hydroxyalkylamide crosslinker from EMS-Chemie AG in Domat/Switzerland. Ave. e.w. = 84
[4]Saturated, carboxylated polyester resin from DSM Resins International. Ave. e.w. = 1600
[5]Titanium dioxide from DuPont Company
[6]Modaflow Powder 2000 from Solutia, Inc.

TABLE 3

| Example | Gel Times, sec. 135° C. | Gel. Times, sec. 200° C. |
|---|---|---|
| 14 | 120 | 20 |
| 15 | 421 | 44 |
| 16 | 863 | 62 |
| 17 | 142 | 17 |
| 18 | 446 | 58 |
| 19 | 766 | 57 |

The above gel time data shows significant reduced time to reach gel point using the tetraoxazoline crosslinker of the invention in comparison with commercially available powder coating crosslinkers. (Ex. 14 vs. 15 and 16). The presence of $TiO_2$ pigment has only minor effect (Ex. 14 vs. 17) on gel time.

The preceding description is for illustration and should not be taken as limiting. Various modifications and alterations will be readily suggested to persons skilled in the art. It is intended, therefore, that the foregoing be considered exemplary only and that the scope of the invention be ascertained from the following claims.

What is claimed is:

1. A compound of the formula:

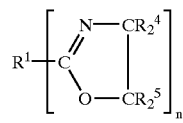

where n is 4 or 6; $R^1$ is a tetravalent or hexavalent group of the formula:

where $R^2$ is H or $C_1$ to $C_6$ linear or branched alkyl; $R^3$ is selected from: $(CH_2)_x$ and its branched isomers where x is 1 to 20; —$C_6H_{10}$—; and

and $R^4$ and $R^5$ are each H or $CH_3$.

2. The compound of claim 1 wherein $R^1$ is tetravalent, $R^2$, $R^4$ and $R^5$ are H, and $R^3$ is $(CH_2)_4$.

3. The compound of claim 1 wherein $R^1$ is tetravalent, $R^2$ is H, $R^3$ is $(CH_2)_4$, $R^4$ is H and $CH_3$ and $R^5$ is H.

4. The compound of claim 1 wherein $R^1$ is tetravalent, $R^2$ is H, $R^3$ is $(CH_2)_4$, $R^4$ is H and $R^5$ is $CH_3$.

5. A curable coating composition comprising:
   a) a carboxyl-functional coreactant polymer; and
   b) a compound having at least four oxazoline or oxazoline derivative groups which are reactive with the carboxyl functionality.

6. The composition of claim 5 wherein b) contains four oxazoline groups.

7. The composition of claim 5 wherein b) contains four methyl-substituted oxazoline derivative groups.

8. The composition of any of claim 5, 6 or 7 wherein the coreactant polymer is polyester.

9. A curable powder resin coating composition comprising:
   a) a carboxyl-functional polyester; and
   b) a compound having a molecular weight less than 1000 containing four or six oxazoline or methyl-substituted oxazoline groups which are reactive with the carboxyl functionality.

* * * * *